United States Patent [19]

Hennessy et al.

[11] Patent Number: 5,219,909
[45] Date of Patent: Jun. 15, 1993

[54] SEMICARBAZIDE/URETHANE STABILIZER

[75] Inventors: Michael J. Hennessy, Vineland, N.J.; Gordon W. Selling, Waynesboro, Va.

[73] Assignee: E. I. Du Pont de Nemours and Company, Wilmington, Del.

[21] Appl. No.: 830,329

[22] Filed: Jan. 31, 1992

[51] Int. Cl.⁵ .................. C08K 5/26; C07C 281/06; C07D 249/08
[52] U.S. Cl. ..................... 524/191; 524/27; 528/62; 548/262.6; 548/264.8; 564/34; 564/37
[58] Field of Search ............ 548/264.8, 262.6; 564/34, 37; 528/62; 524/27, 58, 191

[56] References Cited

U.S. PATENT DOCUMENTS

| | | | |
|---|---|---|---|
| 3,399,167 | 8/1968 | Rosendahl et al. | 260/45.8 |
| 4,447,571 | 5/1984 | Dabi et al. | 524/191 |
| 4,973,618 | 11/1990 | Ulteg | 524/192 |
| 5,028,642 | 7/1991 | Goodrich et al. | 524/27 |

*Primary Examiner*—Paul R. Michl
*Assistant Examiner*—Tae H. Yoon

[57] ABSTRACT

Mixtures comprising semicarbazide/urethane reaction products of 4-amino-1,2,4-triazole, an aliphatic polyisocyanate and a reduced sugar or glycerol are particularly suited for protecting films, fibers, spandex and other polyurethane articles against discoloration due to exposure to fumes, light and heat.

7 Claims, No Drawings

SEMICARBAZIDE/URETHANE STABILIZER

BACKGROUND OF THE INVENTION

1. Field of the Invention

The present invention relates to a novel semicarbazide/urethane mixture which is useful as a stabilizer for polyurethane. More particularly, the invention concerns such a stabilizer which is derived from 4-amino-1,2,4-triazole, an aliphatic polyisocyanate and a reduced sugar or glycerol and is particularly useful as a stabilizer for spandex.

2. Description of the Prior Art

Polyurethanes derived from polyethers or polyesters, especially those intended for use in spandex, require protection against discoloration caused by oxidation, atmospheric fumes, nitrogen oxide gases, exposure to light, and the like. Many stabilizers have been disclosed for use in these polymers. For example, U.S. Pat. No. 3,399,167, Rosendahl et al, discloses 1,1-dialkyl-semicarbazides and 1,1-dialkyl-carbazinic acid esters as stabilizers for polyurethanes. Most of the many semicarbazides disclosed by Rosendahl et al, are derived from asymmetrically substituted dialkyl hydrazines; only one is derived from a triazole, namely the bis-semicarbazide of the reaction of 4-amino-1,2,4-triazole and hexamethylene diisocyanate. However, the present inventors found that this semicarbazide compound is only sparingly soluble in solvents usually employed for dry spinning spandex and therefore is not practically usable for producing spandex.

U.S. Pat. No. 4,973,618, Ultee discloses protecting spandex from discoloration by atmospheric fumes and/or light, with oligomeric additives of 1,000 to 5,000 molecular weight, prepared from polyether glycols, diisocyanates and 1,1-dialkylhydrazines. These oligomers avoid problems of additive extraction during scrubbing, washing and like operations, as was commonly encountered with previously known semicarbazide additives.

Generally, the stabilizers disclosed by Ultee and by Rosendahl et al (except for the bis-semicarbazide derived from 4-amino-1,2,4-triazole) require unsymmetrical dialkylhydrazines for their manufacture. However, unsymmetrical dialkylhydrazines are highly toxic, and the 1,1-dimethylhydrazine, the most commonly used dialkylhydrazine is a flammable, carcinogenic compound that oxidizes to dimethyl nitrosamine, which is an even more powerful carcinogen.

U.S. Pat. No. 5,028,642, Goodrich et al, discloses improved spandex containing zinc oxide and a polyhydroxy additive selected from certain sugars, reduced sugars and/or polyhydroxy urethanes formed from the sugars or reduced sugars and an organic diisocyanate.

The objects of the present invention are to provide a stabilizer for spandex that (a) is soluble in solvents commonly used for dry-spinning spandex, (b) does not require handling of hazardous unsymmetrical substituted dialkylhydrazines and (c) does not require zinc oxide in its formulation.

SUMMARY OF THE INVENTION

The present invention provides a stabilizer composition that is particularly suited for protecting spandex against discoloration by fumes, light and/or heat. The stabilizer comprises a mixture of products which was formed by reacting 4-amino-1,2,4-triazole with an aliphatic polyisocyanate and further reacting with a reduced sugar or glycerol. The mixture preferably comprises semicarbazide/urethane compounds that can be represented by the formula

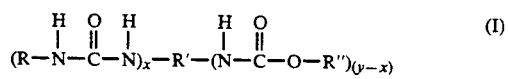

wherein
R is a 1,2,4-triazole moiety connected at the four position,
R' is the moiety obtained by removal of isocyanate groups from the aliphatic polyisocyanate,
R'' is a moiety obtained by removal of hydroxyl groups from the reduced sugar or glycerol which hydroxyl groups reacted with the polyisocyanate,
x is the number of triazole moieties per polyisocyanate molecule that reacted with the isocyanate groups of the diisocyanate, and
y is the number of isocyanate groups per polyisocyanate molecule contained in the polyisocyanate precursor of R, and/or oligomeric products of the reactions and the mixture of reaction products is soluble at room temperature at a concentration of at least 25% by weight in N,N-dimethylacetamide.

The present invention also provides (a) a process for preparing the soluble semicarbazide/urethanes stabilizer mixture and (b) fibers, particularly spandex, and films protected by the stabilizer mixture.

DETAILED DESCRIPTION OF PREFERRED EMBODIMENTS

The present invention is based on the discovery that novel semicarbazide/urethanes derived from 4-amino-1,2,4-triazole polyisocyanates and reduced sugars or glycerol are useful as stabilizers for polyurethane polymers, particularly those intended for the production of spandex elastic yarns; can be produced without using hazardous asymmetrically substituted dialkyl hydrazines; do not require incorporation of zinc oxide in the stabilizer formulation; and are soluble at room temperature in solvents conventionally used in the dry spinning of spandex.

For convenience, in the discussion and examples which follow, the following abbreviations and tradenames are use for the accompanying listed chemical:

| | |
|---|---|
| 4-AT | 4-amino-1,2,4-triazole |
| PICM | 4,4'-methylene-bis(cyclohexylisocyanate) |
| HMDI | hexamethylene diisocyanate |
| IPDI | isopherone diisocyanate |
| TMXDI | alpha, alpha, alpha',alpha'-tetramethylxylylene diisocyanate |
| DMAc | N,N-dimethylacetamide |
| Cyanox | "Cyanox" 1790 antioxidant,1,3,5-tris(4-t-butyl-3-hydroxy-2,6-dimethylbenzyl)-1,3,5-triazine-2,4,6(1H,3H,5H)trione, sold by American Cyanamid |
| DIPAM/DM | copolymer of a 75/25 weight ratio of diisopropylaminoethyl methacrylate and n-decyl methacrylate |

"Spandex", as used herein, has its usual generic meaning; namely, fiber made from long chain synthetic polymer that comprises at least 85% by weight segmented polyurethane.

In accordance with the invention, the novel stabilizer mixtures are prepared by reacting 4-AT with part of the isocyanate groups of an aliphatic polyisocyanate followed by reaction of the remaining isocyanate groups of the polyisocyanate with a polyol. The reaction products are mixtures which comprise semicarbazide/urethane compounds and oligomers of the kind represented by Formulae (I) above, which usually amount to in the range of 40 to 80% of the total weight of the mixture. The mixture may also contain as much as 25% of a bis-semicarbazide of 4-AT and polyisocyanate and smaller amounts of a bis-urethane of reduced sugar or glycerol and polyisocyanate (usually less than 10%).

Various aliphatic polyisocyanates can be used to prepare the products of the present invention, among which are methylene-bis(4-cyclohexylisocyanate) ("PICM"), isopherone diisocyanate ("IPDI") and its oligomers, hexamethylene diisocyanate ("HMDI") and its oligomers, tetramethylxylene diiisocyanate ("TMXDI") and its oligomers, and the like. PICM is preferred because of its cost, its availability and the properties of the products derived from it.

Glycerol and various reduced sugars can be used to prepare products acording to the invention. Among suitable reduced sugars are sorbitol, mannitol, xylitol, adonitol, dulcitol, pentaerythritol, erythritol, threitol, inositol, and the like. Sorbitol is preferred because of its cost, its availability and the properties of the products derived from it. In the discussion that follows, when the term reduced sugars is used, it is intended to include glycerol (even though glycerol conventionally is not considered to be a reduced sugar).

The process of this invention is preferably carried out in two steps. In the first step, 4-AT is reacted with an aliphatic polyisocyanate in a suitable solvent to form semicarbazide groups. Usually, 4-AT is added to the polyisocyanate (rather than vice versa) with vigorous mixing. Molar ratios are controlled so that only a portion of the isocyanate groups of the polyisocyanate are consumed. In the second step, the product of the first step is reacted further with a reduced sugar, so that all of the isocyanate groups remaining after completion of the first step react with the hydroxyl groups of the reduced sugar to form urethane groups in the final product. This method insures maximum utilization of the 4-AT. The desired product contains both semicarbazide and urethane groups. The presence of semicarbazide and urethane groups in the product is confirmed by positive fast atom bombardment mass spectrometry.

Molar ratios for the 4-AT, polyisocyanate and reduced sugar starting materials are preferably in the range of 2/2/1 and 1/1/1, when diisocyanate is employed as the polyisocyanate. The present inventors found that when 4-AT, PICM and sorbitol, the preferred starting materials, are employed in accordance with the invention, whether in the 2/2/1 or 1/1/1 ratios (on a molar basis), the resultant products are about equally effective in stabilizing spandex against fumes, light and heat. If aromatic diisocyanates, which are outside the invention, are substituted for the aliphatic diisocyanates, inferior stabilization of spandex is obtained.

Alternative, less desirable methods, can produce stabilizer mixtures that are similar to the products of the present invention. In one alternative process, the reduced sugar and polyisocyanate are reacted first and then the 4-AT is introduced into the system. In another alternative method, the 4-AT, the polyisocyanate and the polyol are all reacted together in the presence of a catalyst, such as an organotitanate. In each alternative methods, there is less assurance of reacting all of the 4-AT. Incomplete reaction of the 4-AT results in poorer stabilization performance of the mixture in polyurethane polymers. Use of catalysts also introduces uncertainies with regard to further possible effects of the catalysts on subsequent processing and/or end-use properties.

Suitable solvents for use in the process of this invention are polar and nonprotic. Among such solvents are N,N-dimethylacetamide (DMAc), N,N-dimethylformamide and the like. DMAc is preferred.

In the process of the invention in which 4-AT and polyisocyanate are reacted first and then remaining isocyanate groups are reacted with the reduced sugar, the first step can be carried out at temperatures in the range of about 50° C. to the boiling temperature of the solvent in which the reaction is carried out (e.g., 164°πC. in the case of DMAc). Temperatures of 80° C. to about 120° C. are preferred. At temperatures below 80° C., the reaction mass is usually too viscous for conveneient thorough mixing. At temperatures above 120° C., undesirable color may be encountered in the product. Reaction times, which of course depend on the temperature of the reaction, usually are in the range of 1 to 24 hours, which time is controlled to assure complete reaction of the 4-AT starting material. Temperatures in the range of about 50° C. to the boiling temperature of the solvent and reaction times of 1 to 24 hours are generally satisfactory for the second step of the reaction.

To function effectively in polyurethane fibers and films, particularly in spandex, the concentration of the mixture of semicarbazide/urethane reaction products of the invention is usually in the range of 0.25% and 10%, based on the weight of the polyurethane polymer. Concentrations in the range of 1-5% are preferred.

The additives mixtures of the invention can be incorporated into segmented polyurethane polymers or into spandex formed from the polymers, by conventional techniques. For example, a concentrated solution of the additive mixture can be prepared in the same solvent as is used to prepare the polymer solution; optionally, the solution can be mixed with other conventional additives; and then all can be mixed with the polymer solution. Because semicarbazide/urethanes of this invention are soluble in conventionally used spandex spinning solvents (e.g., DMAc), their incorporation into spinning solutions is readily accomplished without the formation of undesirable particles that could plug spinnerets.

Other additives, fillers, plasticizers, pigments and the like which are conventionally used with segmented polyurethanes, can be used with the additives of this invention. Examples of such conventional additives include: (a) hindered phenolic antioxidants, such as "Irganox" 245, "Irganox" 1010 and "Cyanox"; (b) hindered amine light stabilizers, such as "Tinuvin" 622, "Tinuvin" 765, "Tinuvin" 770, polymeric tertiary-aminoalkyl acrylates and methacrylates, such as DI-PAM/DM and reaction products of diisocyanates and tertiary amine-containing diols; (c) ultraviolet screening agents such as "Tinuvin" 327, "Tinuvin" 328, "Tinuvin" 234, "Cyasorb" 1164, "Sandovar" VSU, and "Cyasorb" UV 531; (d) tack-reducing agents, such as silicon oil, mineral oil and metal soaps, such as calcium stearate, magnesium stearate and lithium stearate; (e) pigments such as zinc oxide, barium sulfate and titanium dioxide; and the like.

Polyurethane polymer containing a stabilizer mixtures product of the invention can be formed into various articles such as fibers, films and molded shapes.

Test Methods

Several tests were employed in the examples below to measure the effectiveness of the additives of this invention, in stabilizing spandex and the polyurethane polymer from which the spandex was formed against discoloration due to light, fumes or heat. All tests were conducted on fiber or film samples made from solutions of polyurethane polymer containing the additives to be tested.

Polymer Sample Preparation

To illustrate the invention in the examples below, a segmented polyether-based polyurethaneurea polymer solution was used to form spandex (i.e., fiber) and/or film samples. The polymer solution was prepared by the general procedure described by Hunt, U.S. Pat. No. 3,428,711. Bis(p-isocyanatophenyl)methane (MDI) and poly(tetramethyleneether)glycol of 1800 number average molecular weight were intimately mixed in a molar ratio of 1.63:1 and maintained at a temperature in the range of 80° to 90° C. for about 90 to 100 minutes, to yield an isocyanate-terminated polyether/urethane (i.e., a "capped glycol"). The latter, after having been cooled to 60° C., was mixed with DMAc to provide a solution containing about 45% solids. Then, with vigorous mixing, the capped glycol was reacted for 2 to 3 minutes at a temperature of about 75° C. with a DMAc solution containing a mixture of diethylamine chain-terminator and a 90/10 molar ratio of ethylene diamine and 1,3-cyclohexylene diamine chain-extenders. The resulting solution of segmented polyurethane/urea contained approximately 37% solids and had a viscosity of about 2,500 poises at 40° C. The thusly produced polymer solution was then, by conventional techniques, dry spun into coalesced, 4-filament, 44-dtex yarns or cast onto clear polyester film (i.e., "Mylar" sold by E. I. du Pont de Nemours & Co.) to form 0.01-inch (0.025-cm) thick sample film layer.

Polymer solutions for preparing samples of dry-spun yarns of clear spandex contained (based on the final weight of spandex without finish) (a) 1.5% of "Cyanox" 1790 antioxidant, (b) 2.0% of DIPAM/DM copolymer, (c) 0.6% of a silicone oil and d) 1.6% of the particular additive mixture being tested. Polymer solutions for spinning yarns of "bright" spandex contained the same additives as clear spandex yarns, but also contained 3% of zinc oxide. Polymer solutions for spinning yarns of "dull" spandex contained the same additivies as clear spandex yarns, but also contained 2% of titanium dioxide.

Samples of the dry-spun yarns were given a simulated solvent finishing treatment before being subjected to exposure testing. The simulated finishing treatment consisted of (a) a 90-second immersion of the yarn in perchloroethylene maintained at 45° C., followed by air drying and a simulated dyeing treatment in water having a pH of 5 (sodium pyrophosphate buffer) for 30 minutes at 90° C., or (b), the same as (a), except that the simulating dyeing treatment also included 4.5 grams of Duponol EP (a sulfate detergent sold by E. I. du Pont de Nemours & Co.) per liter of water.

Exposure Tests

The effects of all exposure tests were determined by means of measurements of the amount of discoloration undergone by the test samples as a result of the exposure. Discoloration was measured as a change in "b" value (i.e., "delta b") by means of differential colorimetry (e.g. with a Model D-25-3 Differential Colorimeter manufactured by Hunter Associates Laboratory, Inc. of Reston, Va.) which had been calibrated against the manufacturer's standard reference plates. For these measurements, yarn test samples were wound under low tension on an aluminum card that measures approximately 8 by 11 by 0.2 centimeters, to form a layer of about 3–4 millimeters thick. Film sample discoloration was measured directly on the cast film.

Tests in which samples were exposed to combustion fumes (labeled "fume" in the tables below) were conducted in accordance with Test Method 23-1962 of AATCC (American Association of Textile Chemists and Colorists). An atmospheric fume chamber Model 6528 made by United States Testing Company, Inc. of Hoboken, N.J., was employed. For exposures to nitrogen oxide with ultraviolet light (labeled "NO2/UV" in the tables below), a Scott Controlled Atmosphere tester was used. Air containing 1,000 ppm (parts per million) of nitrogen dioxide was introduced at a approximately 3 liters per minute. Light was supplied to the tester by eight "daylight" and four "black" fluorescent tubes (e.g., type F30T8 and FTO38BL manufactured by General Electric Co.). A fan mixed and circulated the gases in the test chamber. For exposure to ultraviolet light (labeled "UV" in the tables below), tests were conducted in the presence of water, in an Atlas Series C "Weather-ometer", made by Atlas Electric Devices Co. of Chicago, Ill. In the Weather-ometer, samples are exposed to a xenon light having a spectrum resembling that of sunlight. For exposure to $NO_2$ gas alone (labeled "NO2" in the tables below), an Atlas Gas Exposure chamber, made by Atlas Electric Devices Co. of Chicago, Ill., was used. The temperature and relative humidity were allowed to remain at or near room conditions. The chamber was supplied with air containing approximately 1000 ppm of $NO_2$ at a rate of approximately 3 liters/minute. Thermal degradation tests (labeled "therm" in the tables below were performed in an oven in which the samples were exposed to air at 175° C.

The duration of each exposure test in hours for the samples described in the Examples was as follows:

| Sample | Fume | NO2 | NO2/UV | UV | Therm |
| --- | --- | --- | --- | --- | --- |
| Clear Spandex | 72 | 72 | 48 | 24 | 1.0 |
| Bright Spandex | 24 | 120 | 48 | 24 | 0.5 |
| Dull Spandex | 48 | 72 | 48 | 24 | 1.5 |
| Clear Film | 114 | 114 | 114 | 114 | 1.0 |

EXAMPLES

The examples which follow are illustrative of the invention but are not intended to limit its scope, which is defined by the claims. The results reported herein are believed to be representative, but do not constitute all the runs involving the indicated ingredients. In the examples, samples designated with Arabic numerals contain stabilizer mixtures in accordance with the invention, and those designated with upper case letters are comparison samples outside the invention from which such stabilizer mixtures are omitted.

Examples 1 and 2 describe preparation of stabilizer mixtures of the invention and their performance in spandex yarns. Yarn exposure data are summarized in Table I. Preparation of additional embodiments of the invention is described in Examples 3–15. Exposure-test performance of films containing the stabilizer mixtures of Examples 1–15 are summarized in Table II.

EXAMPLES 1 & 2

A 2-liter flask, equipped with a nitrogen inlet, means for drawing a vacuum, thermocouple, heating mantle, reflux condenser, mechanical stirrer and a valved bottom outlet to a 5-liter lower flask, was charged with 760 g of dimethylacetamide (DMAc). The DMAc was heated to about 50° C. and 184.6 g (2.196 mol) of 4-AT and 576 g, (2.196 mol) of PICM ("Desmodur" W supplied by Mobay Chemical Co.) were added. The flask was evacuated to about 10 mm of Hg pressure and then the flask was restored to atmospheric pressure with nitrogen. This step was repeated twice. The flask was then heated to 105° C. and maintained at that temperature for about 18 hours. The charge was dropped from the top flask in five, approximately equal portions, one hour apart, into the lower 5-liter flask, which was equipped in the same way as the top flask and contained 400 g of DMAc and 400 g (2.196 mol) of sorbitol maintained at about 100 ° C. After the addition was completed, the contents of the lower flask were heated at 100° C. for 4 hours and then cooled to room temperature. The resulting solution contained a semicarbazide-/urethane stabilizer of the invention. The molar ratio of 4-AT/PICM/sorbitol in Example 1 was 1/1/1. For Example 2, the procedure of Example 1 was repeated except that the molar ratio of 4-AT/PICM/sorbitol was adjusted to 2/2/1.

Clear, bright, and dull spandex yarns were formed with the semicarbazide/urethane stabilizer mixture of Example 1 amounting to 1.6% by weight of the spandex. A bright yarn also was made with the semicarbazide/urethane stabilizer mixture of Example 2. Comparison spandex yarn samples A, B and C omitted the semicarbazide/urethane stabilizer mixtures. In another exposure test, yarns of clear spandex corresponding to example 1, comparison sample A and another comparison, sample D were tested together. For comparison sample D, the additional stabilizer was a bis-semicarbazide prepared from 4-AT and HMDI (i.e., without a polyol). Table I summarizes exposure tests results for these yarns.

TABLE I

| Sample | Fume | NO2 | NO2/UV | UV | Therm |
|---|---|---|---|---|---|
| Clear Spandex | | | | | |
| A | 5.1 | 7.8 | 5.7 | 11 | 3.7 |
| 1 | 2.2 | 3.9 | 3.2 | 12 | 2.3 |
| Bright Spandex | | | | | |
| B | 6 | 7.9 | 7.2 | 8.8 | 5.8 |
| 1 | 2.7 | 4.3 | 4 | 7 | 3.1 |
| 2 | 3.3 | 5.8 | 4.5 | 6.9 | 3.4 |
| Dull Spandex | | | | | |
| C | 7.1 | 6 | 5.7 | 4.9 | 4.7 |
| 1 | 4.1 | 3.9 | 6.1 | 4.9 | 2.2 |
| Clear Spandex | | | | | |
| A | 10.7* | 5.0 | 5.5* | 8.6 | 6.0+ |
| D | 7.0* | 4.7 | 5.3* | 9.1 | 2.4+ |
| 1 | 5.3* | 6.0 | 3.8* | 6.2 | 2.3+ |

Notes:
*24 hour exposure test.
+0.2 hour exposure test.

The results of the tests summarized in Table I demonstrate the value of the semicarbazide/urethane stabilizer mixtures of the invention in protecting spandex yarns from excessive discoloration by exposure to fumes, nitrogen oxide, ultraviolet light and heat.

EXAMPLES 3 THRU 12

Examples 3 through 12 were prepared in the same manner as Example 1 in apparatus equipped as in Example 1 but with an upper flask of 0.5-liter volume and a lower flask of 1-liter volume. The quantities used in preparing the stabilizer mixtures are summarized in Table II, as are the data for Examples 1 and 2. All weights are in grams.

TABLE II

Stabilizer Mixture Preparations

| Ex. | Upper Flask | | | | Lower Flask | | | Note |
|---|---|---|---|---|---|---|---|---|
| | 4-AT | DMAc | Polyisocyanate | | DMAc | Polyol[3] | | |
| | | | Type | Weight | | Type | Weight | |
| 1 | 184.6 | 760 | PICM | 576 | 400 | So | 400 | — |
| 2 | 46.15 | 190 | " | 144 | 50 | " | 50 | — |
| 3 | " | " | " | " | 75 | Pe | 74.73 | 1 |
| 4 | " | " | " | " | 67 | Er | 67.03 | — |
| 5 | " | " | " | " | 83.5 | Ad | 83.52 | — |
| 6 | " | " | " | " | 50.5 | Gl | 50.52 | — |
| 7 | " | " | " | " | 100 | Du | 100 | 2 |
| 8 | " | " | " | " | 83.5 | Xy | 83. | — |
| 9 | " | " | " | " | 100 | Ma | 100 | 2 |
| 10 | " | 138 | HMDI | 92.3 | 100 | So | 100 | — |
| 11 | " | 168 | IPDI | 122.0 | " | " | " | — |
| 12 | " | 180 | TMXDI | 134 | " | " | " | — |

Notes:
1. Bottom flask was heated to 150° C. to dissolve the pentaerythritol.
2. Bottom flask was heated to 160° C. to dissolve polyol.
3. So = sorbitol; Pe = pentaerythritol; Er = erythritol; Ad = adonitol; Gl = glycerol; Du = dulcitol; Xy = xylitol; Ma = mannitol.

EXAMPLES 13

This example describes a semicarbazide/urethane stabilizer mixture of the invention prepared from 4-AT, an oligomeric diisocyanate and sorbitol.

A 500-ml flask, equipped with a nitrogen/vacuum line, thermocouple, heating mantle, reflux condenser, mechanical stirrer and a bottom outlet attached with a tube and valve to a lower flask of one-liter volume, was charged with 255 g of DMAc. The DMAc was heated to about 50° C. Then, 92.3 g (0.549 mol) of 4-AT and 163 g (0.823 mol) of "Desmodur" 3300 (an oligomer of HMDI, sold by Mobay Corporation) were added. The flask was evacuated to about 10 mm of Hg pressure and the vacuum released with nitrogen. This step was repeated twice. The flask and its contents were heated to 105° C. and held at that temperature for about 18 hours. The charge was then fed in five, approximately equal portions, one hour apart, into the lower one-liter flask, which initially contained 50 g of DMAc, and 50 g (0.275 mol) of sorbitol maintained at about 100° C. The lower flask which was equipped with the same devices as the upper flask. Heating of the contents of the lower flask at 100° C. was continued for 4 hours. The contents were then cooled to room temperature to yield a solution of semicarbazide/urethane stabilizer mixture of the invention.

The solutions of the semicarbazide/urethane stabilizer mixtures of Examples 1-14 were incorporated into polyurethane polymer and cast into clear films for exposure testing. The films were dried overnight at ambient temperature in a nitrogen environment before being subjected to the various exposure tests in accordance with the test methods described above. The film samples were not given a simulated finishing treatment prior to testing. Results of the exposure tests are summarized in Table III, which lists the discoloration (i.e., "delta b" values) experienced by the samples in the tests. Comparison sample E contained no semicarbazide/urethane stabilizer mixture.

TABLE III

| Sample | Exposure tests of clear films | | | | |
| --- | --- | --- | --- | --- | --- |
| | Fume | NO2 | NO2/UV | UV | Therm |
| E | 20.0 | 8.6 | 12.2 | 22.0 | 17.7 |
| 1 | 8.3 | 5.3 | 3.7 | 6.3 | 2.9 |
| 3 | 6.9 | 5.4 | 2.1 | 5.8 | 5.9 |
| 4 | 5.4 | 5.2 | 2.0 | 7.0 | 2.7 |
| 5 | 7.7 | 4.5 | 1.9 | 6.2 | 2.8 |
| 6 | 8.5 | 2.4 | 2.5 | 7.0 | 3.0 |
| 7 | 9.0 | 5.6 | 1.8 | 6.3 | 3.9 |
| 8 | 2.4 | 2.5 | 1.6 | 6.3 | 3.0 |
| 9 | 4.6 | 1.0 | 2.8 | 5.9 | 3.3 |
| 10 | 5.4 | 2.4 | 2.6 | 7.7 | 4.2 |
| 11 | 4.5 | 5.3 | 2.8 | 6.3 | 4.2 |
| 12 | 4.2 | 4.8 | 1.8 | 6.2 | 6.2 |
| 13 | 9.0 | 3.5 | 2.5 | 6.3 | 4.6 |

When aromatic diisocyanates, e.g., methylene-bis-(4-phenyl-isocyanate), toluene diisocyanate, were substituted for the aliphatic diisocyanates in the preparation of the semicarbazide/urethane stabilizer mixture, exposure tests showed that the resultant mixtures provided polyurethanes with poorer protection against fumes and nitrogen oxide than did the stabilizers mixtures of the invention. Also, when polyols outside the invention, e.g., polyethylene glycol, were substituted for the reduced sugars or glycerol required by the invention, exposure tests with samples containing showed the resultant mixtures to be inferior stabilizers compared to those of the invention.

We claim:

1. A stabilizer composition, particularly suited for protecting spandex against discoloration by fumes, light and heat, the stabilizer comprising a mixture of products formed by first reacting 4-amino-1,2,4-triazole with an aliphatic polyisocyanate and then reacting the products of the first reaction with a reduced sugar or glycerol, the mixture having molar ratios of 4-amino-1,2,4-triazole to aliphatic polyisocyanate to reduced sugar or glycerol in the range of 1:1:1 to 2:2:1 and the polyisocyanate being selected from the group consisting of methylene-bis(4-cyclohexylisocyanate), isophorone diisocyanate and its oligomers, and tetramethylxylylene diisocyanate and its oligomers, the mixture of reaction product being soluble at room temperature at a concentration of at least 25% by weight in N,N-dimethylacetamide.

2. A stabilizer composition according to claim 1 wherein the mixture comprises semicarbazide/urethane compounds represented by the formulae

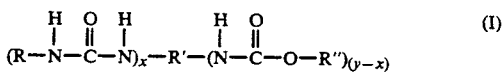

$$(R{-}N{-}C{-}N)_x{-}R'{-}(N{-}C{-}O{-}R'')_{(y-x)} \quad (I)$$

with H, O, H above the first group and H, O above the second (H—N—C—N and N—C—O).

wherein
R is a 1,2,4-triazole moiety connected at the four position,
R' is the moiety obtained by removal of isocyanate groups from the aliphatic polyisocyanate,
R" is a moiety obtained by removal of hydroxyl groups from the reduced sugar or glycerol which hydroxyl groups reacted with the polyisocyanate,
x is the number of triazole moieties per polyisocyanate molecule that reacted with the isocyanate groups of the polyisocyanate, and
y is the number of isocyanate groups per polyisocyanate molecule contained in the polyisocyanate precursor of R, and/or oligomeric products of the reactions.

3. A stabilizer composition according to claim 2 wherein the polyisocyanate is methylene-bis(4-cyclohexylisocyanate) and the reduced sugar is sorbitol.

4. An article of polyurethane polymer containing 0.25 to 10 percent by weight of the polymer of a stabilizer mixture in accordance with claim 1.

5. An article according to claim 4 wherein the article is spandex and the stabilizer mixture amounts 1 to 5% of the spandex weight.

6. A process for preparing a semicarbazide/urethane stabilizer mixture comprising in sequence the steps of
reacting 4-amino-1,2,4-triazole and an aliphatic polyisocyanate in a polar aprotic solvent for a sufficient time and at a sufficient temperature in a molar ratio that assures only some of the isocyanate groups of the polyisocyanate are reacted,
the polyisocyanate being selected from the group consisting of 4,4'-methylene-bis(cyclohexylisocyanate), isopherone diisocyanate and its oligomers, and tetramethylxylylene diisocyanate and its oligomers,
reacting the products of the preceding step in the solvent, for a sufficient time and at a sufficient temperature with a reduced sugar or glycerol in a sufficient quantity to assure reaction of the isocyanate groups that were not reacted in the preceding step with hydroxyl groups of the reduced sugar or glycerol,
with molar ratios of 4-amino-1,2,4-triazole to aliphatic polyisocyanate to reduced sugar or glycerol in the range of 1:1:1 to 2:2:1 and
the reactions being performed at a temperature in the range of 50° to 164° C. for 1 to 24 hours.

7. A process according to claim 6 wherein the polyisocyanate is methylene-bis(4-cyclohexylisocyanate), the reduced sugar is sorbitol and the solvent is dimethylacetamide.

* * * * *